United States Patent [19]

Schmidtberger

[11] Patent Number: 5,180,679
[45] Date of Patent: Jan. 19, 1993

[54] DIAGNOSTIC AGENT AND A METHOD FOR THE DETERMINATION OF APOLIPOPROTEIN B

[75] Inventor: Rudolf Schmidtberger, Marburg, Fed. Rep. of Germany

[73] Assignee: Behringwerke Aktiengesellschaft, Marburg, Fed. Rep. of Germany

[21] Appl. No.: 254,062

[22] Filed: Oct. 6, 1988

[30] Foreign Application Priority Data

Oct. 8, 1987 [DE] Fed. Rep. of Germany ....... 3734015

[51] Int. Cl.$^5$ ................. G01N 33/543; G01N 33/546; G01N 33/547; G01N 33/557
[52] U.S. Cl. .................... 436/518; 436/517; 436/533; 436/534
[58] Field of Search .............. 436/533, 517, 534, 826, 436/518, 520; 530/359, 846, 387, 810, 815, 816

[56] References Cited

U.S. PATENT DOCUMENTS

| | | | |
|---|---|---|---|
| 4,376,110 | 3/1983 | David et al. | 436/513 |
| 4,778,752 | 10/1988 | Curtiss et al. | 435/7.92 |
| 4,970,144 | 11/1990 | Fareed et al. | 435/7.93 |

FOREIGN PATENT DOCUMENTS

| | | |
|---|---|---|
| 0262854 | 4/1988 | European Pat. Off. |
| WO86/05493 | 9/1986 | PCT Int'l Appl. |

OTHER PUBLICATIONS

Cambiaso, et al. 1977. Particle counting immunoassay (PACIA) I. General Method for determination of antibodies . . . J. Immunolog. Meth. 18 33.

Rosseneu, et al. 1981. Standardization of immunoassays for quantitation of plasma protein Apo B. Anal. Biochem. 116 204.

Masson et al. 1981. Particle counting immunoassay: An automated non-radioisotopic Immunoassay Method . . . IV: Immunoassays for the 80's. A. Voller, ed. Univ. Park Press. pp. 35–41.

Becker, W., "Determination of Antisera Titres Using the Single Radial Immunodiffusion Method," Immunochemistry, vol. 6: 539–546 (1969).

Havel, R. et al., "The Distribution and Chemical Composition of Ultracentrifugally Separated Lipoproteins in Human Serum", J. Clin. Invest., vol. 34: 1345–1353 (1955).

Chemical Abstract No. 181710Z, vol. 102, No. 21, May, 1985.

Chemical Abstract, No. 75106p, vol. 104, No. 9, Mar., 1986.

*Primary Examiner*—David Saunders
*Attorney, Agent, or Firm*—Finnegan, Henderson, Farabow, Garrett and Dunner

[57] ABSTRACT

An agent for the determination of apolipoprotein B in blood, plasma or serum by an agglutination method, containing a dispersion of particles to which antibodies against Apo B are bound, as well as an agglutination method, are described.

4 Claims, 1 Drawing Sheet

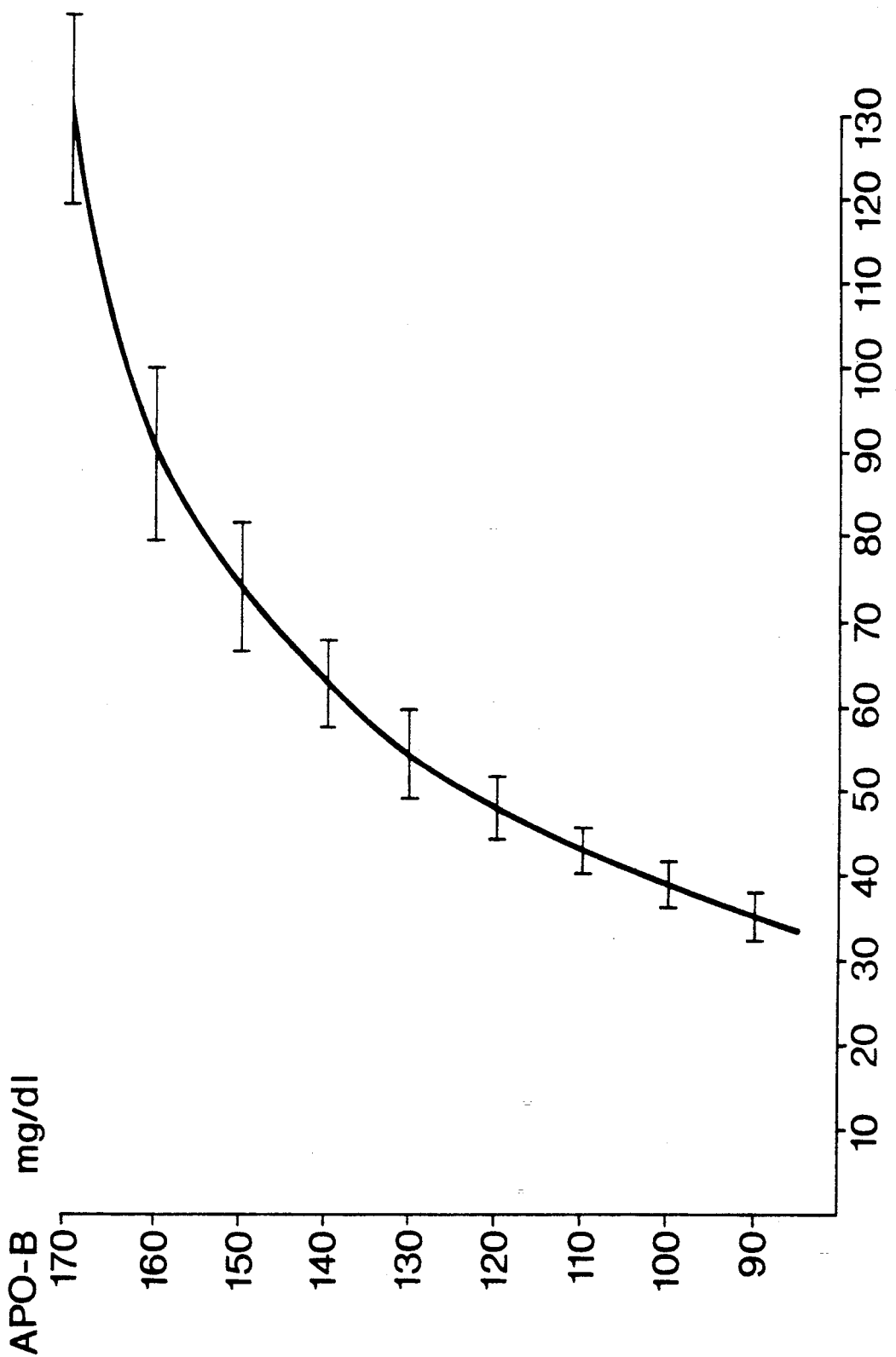

DIAGNOSTIC AGENT AND A METHOD FOR THE DETERMINATION OF APOLIPOPROTEIN B

A diagnostic agent containing a dispersion of particles to which antibodies against apolipoprotein B are bound, and a method using this agent for the determination of apolipoprotein B are described.

The transport of the intrinsically water-insoluble lipids in human metabolism takes place in the form of the so-called lipoproteins. These are complexes composed of proteins and lipids and, in recent years, the class of them which has a low density, called the low-density lipoproteins (LDL), have been recognized as an indicator for coronary disease.

The fact that, in contrast to the other lipoproteins, the only protein component contained in the LDL class is apolipoprotein B has been utilized for an immunochemical determination in the form of a (nephelometric) turbidity reaction and in a combination of separation of LDL from the other lipoproteins by immunoadsorption and subsequent determination of a suitable component of the lipids (DE 3,215,310). However, equipment with appropriate apparatus is necessary for this method.

Hence there has been a need for a straightforward method for the determination of apolipoprotein B.

It has been found, surprisingly, that an agglutination reagent can be prepared for the immunological determination of apolipoprotein B, which allows rapid determination of this protein without elaborate apparatus and can advantageously be used with lipemic samples as well as whole blood, which does not need to be worked up to plasma of serum.

The invention relates to an agent for the determination of apolipoprotein B (Apo B) in blood, plasma or serum by an agglutination method, containing a dispersion of particles to which antibodies against Apo B are bound.

An antibody against Apo B can be bound to the particles by adsorption or covalency or else via biofinity binding, for example by staphylococcus aureus protein A which is applied to the particles first. The antibody-loaded particles are prepared as a dispersion and, where appropriate, mixed with additives such as proteins or detergents in order to prevent spontaneous agglutination.

An agent of this type can contain, in an aqueous medium, particles which are mineral in nature, such as bentonite, or are composed of synthetic globules such as latices having a diameter of 40 to 1200 nm, or of cross-linked polysaccharides or else of erythrocytes whose surface has been chemically treated to make it insensitive to differences in the osmotic conditions in the surrounding solutions.

The amount of antibody is preferably selected such that, where the concentration of Apo B is high in clinical terms, the agglutination occurs at a later time than where the concentration is lower.

The invention also relates to a method for the determination of the concentration of Apo B in a sample of blood, plasma or serum, entailing the sample being mixed with a dispersion of particles to which antibodies against apolipoprotein B are bound, the time until agglutination takes place being determined, and the concentration of Apo B being taken from a reference curve.

FIG. 1 shows a typical reference curve. The amount of Apo B is plotted on the vertical axis, and the measured time of agglutination is plotted on the horizontal. The lines drawn on the curve represent the range of variation of the measured times.

The loading of the particles and the mixing ratio of dispersion and sample are preferably selected such that the mixture agglutinates after two minutes when the sample contains 170 mg of Apo B in 100 ml. Agglutination of the particles in 2 minutes or less then means that the concentration of Apo B is less than 170 mg/100 ml and is thus in the normal clinical range, whereas no agglutination after two minutes have elapsed indicates an elevated Apo B concentration, i.e. one above the normal clinical range.

A suitable antibody can be raised by immunization of a suitable animal species with human Apo B and can be obtained from the serum of the particular animal(s) by known methods, for example by precipitation, by ion exchange chromatography or gelfiltration or by a combination of such methods. If monoclonal antibodies are used, it is necessary to select at least two clones which secrete antibodies against two spatially separated epitopes of Apo B, with these monoclonal antibodies being bound to the particles in a suitable ratio of amounts, for example one to be determined experimentally.

The amount of the antibody(ies) with a particular titre which is bound to a defined amount of particles is crucial for the time at which agglutination occurs. It is selected such that, at a concentration of Apo B which is predetermined, for example, by a standard, agglutination takes place at an earlier time when few antibodies, and at a later time when more antibodies, are bound to the particles.

Preferred embodiments of the diagnostic agent contain 5 to 15, preferably 8 to 10 mg/ml of dispersed polystyrene latex having particle sizes of from 200 to 800, preferably 500 to 700, nm and antibodies in a concentration of 2.2 to 3.3, preferably 2.5 to 2.7, mg/ml with titre units of 4 to 6, preferably 5. The definition of a titre unit as 1 mg of Apo B/ml of antiserum for radial immunodiffusion is described in Immunochemistry 6, 539–546 (1969), in particular on page 540 in Equation (3).

A particularly preferred embodiment of the diagnostic agent contains 9 mg/ml of polystyrene latex having a particle size of 600 nm, as well as rabbit IgG antibodies in a concentration of 2.6 mg/ml with a titre of 5 units/ml.

The loading of the particles with antibody is expediently chosen such that, at a concentration of 150 mg/100 ml of Apo B, agglutination occurs after 75 seconds. To adjust the diagnostic agent to this, different amounts of antibody are bound to aliquots of particles, and the agents prepared therefrom are allowed to react with a standard of 150 mg/100 ml of Apo B. The agents which agglutinate with the standard after 70 to 80 seconds provide an indication of the amount of antibody required for binding to the particles in order to achieve agglutination after 75 seconds. The described indicative experiment for the preparation of the agent should be repeated with every other antibody preparation if it differs in the titre, having been obtained from the same animal species, or where the titre is the same and it has been obtained from a different animal species, or where both circumstances differ.

The diagnostic agent prepared in the manner described is additionally tested with other standards of Apo B, i.e. those with concentrations lower and higher than 150 mg/100 ml, and the dependence of the agglutination time on the concentration is determined therefrom. An example of a standard curve obtained in a method of this type is depicted in the Figure. It is possible with the aid of a reference curve of this type to determine Apo B quantitatively within the concentration range predetermined by the curve.

The invention is explained in more detail by the example which follows, without intending to restrict it thereto, however.

EXAMPLE

1. Diagnostic agent

1.1 Antibodies against Apo B

The lipoproteins of density class 1.019–1.063 were obtained from human serum by ultracentrifugation (Havel, R. J., Eder, H. A. and Gragdon, J. H. (1955) J. Clin. Invest. 34, 1345). The LDL thus obtained were used to raise antibodies against the protein component, the apolipoprotein B, in rabbits. The immunization of the animals was continued until an average titre of 19 units/ml was measured in samples of serum taken from these animals. A pool of serum from several animals was dialyzed against 30 mmol/l of sodium phosphate buffer pH 7.0. The gammaglobulin fraction was then obtained by chromatography on DEAE-cellulose DE 32 (Whatman) which had been equilibrated with the same buffer. This entailed the column eluate containing the gamma-globulins being mixed with solid ammonium sulfate to 50% saturation. The gamma-globulins contained in the precipitate were freed of ammonium sulfate by gelfiltration and simultaneously converted into a solution which contained 50 mmol/l of NaCl, 100 mmol/l of glycine and 15 mmol/l of sodium azide. the pH of which had been adjusted to 8.2 with NaOH. The protein concentration in the solution was then brought to 50 mg/ml by ultrafiltration. In parallel with this, a human albumin solution was converted into the same NaCl/glycine solution by gel-filtration. It then had a protein content of 120 mg/ml.

1.2 Latex agglutination reagent 2.0 ml of gamma-globulin solution and 4.1 ml of albumin solution were mixed and made up to 20.4 ml with NaCl/glycine solution. The solution was then heated at 56° C. for 30 min. The solution pretreated in this way was then mixed, whilst stirring, with a dispersion of 20 mg/ml of polystyrene latex particles of 600 nm diameter in NaCl/glycine solution. A total of 17.5 ml of the latex dispersion were added at a rate of 1 ml/h.

2. Method for the determination of apolipoprotein B

2.1 Construction of a standard Curve

Human serum freshly obtained by spontaneous coagulation was centrifuged at 500,000×g for 30 min. The chylomicrons floating after this were aspirated off and discarded. The serum clarified in this way was mixed with sodium chloride to a density of 1.063 and then centrifuged at 500,000×g for 30 min. The contents of the centrifuge tube were divided into an upper LDL-rich and a lower LDL-poor fraction. The Apo B content in both fractions was determined immunochemically:

upper fraction: 234 mg/100 ml
lower fraction: 38 mg/100 ml

The solutions having graduated Apo B contents required for construction of the calibration curve were obtained by mixing defined volumes, determined by calculation, of the two solutions. 20 µl of a human serum containing 150 mg/100 ml of Apo B produced agglutination after 75 sec. when reacted with 20 µl of latex reagent.

2.2 Comparative determination of Apo B in whole blood, plasma and serum from the same donor Blood from a healthy male donor was collected in a receiver containing sodium citrate. One third of the blood were left as whole blood. The remaining two thirds was centrifuged to remove the formed elements of the blood. The plasma obtained as the supernatant was divided in two. One half of the plasma was mixed with 2 IU of thrombin/ml of plasma and, after the coagulation process was complete, precipitated fibrin was removed by centrifugation. The serum obtained as the supernatant from the centrifugation was decanted off and then investigated, comparing with whole blood and plasma. Taking account of the hematocrit of 43 previously determined for the whole blood, 35 µl of whole blood, 20 µl of plasma and 20 µl of serum were each reacted with 20 µl of latex reagent. The agglutination times were found to be

| | |
|---|---|
| Whole blood | 63 sec. corresponding to 140 mg of Apo B/100 ml |
| Plasma | 59 sec. corresponding to 136 mg |
| Serum | 55 sec. corresponding to 132 mg |

For comparison with this, the Apo B content was determined using the Behring nephelometer analyzer. 137 mg of Apo B/100 ml of serum was found in this nephelometric determination.

2.3 Comparative determination of Apo B in lipemic and nonlipemic serum samples from the same donor Serum obtained from lipemic plasma by inducing coagulation with 2 IU/ml of thrombin was centrifuged at 504,000×g (Beckman centrifuge, Rotor 70 T1) for 30 minutes. After the chylomicrons had been removed by syphoning of the upper cloudy zone, the contents of the centrifuge tube were remixed and subjected to the latex assay, comparing with a sample of the uncentrifuged lipemic serum. Both samples agglutinated at the same time, namely after 95 sec., corresponding to 162 mg of Apo B/100 ml, as was read off the standard curve.

I claim:

1. A method for the determination of the concentration of Apo B in a sample of blood, plasma or serum, which comprises steps of
   (i) mixing the sample with a dispersion of particles to which antibodies against apolipoprotein B are bound,
   (ii) determining the time until agglutination takes place, and
   (iii) calculating the relevant concentration of Apo B from a reference curve.

2. The method as claimed in claim 1, wherein the amount of antibody which is bound to the particles, and the mixing ratio of dispersion and sample, are selected such that the mixture agglutinates after about 2 minutes when the sample contains 170 mg of Apo B in 100 ml, and wherein it does not agglutinate when the sample contains more Apo B.

3. The method claimed in claim 1, wherein in step (i), the amount of antibody is selected such that, where the concentration of Apo B is above the normal clinical range, agglutination occurs at a later time than the agglutination where the concentration is in the normal clinical range.

4. The method of claim 1, wherein, in step (i), said dispersion of particles comprises 5 to 15 mg/ml of dispersed polystyrene latex having a particle size of from 200 to 800 nm, and wherein said antibodies are present in a concentration of 2.2 to 3.3 mg/ml with a titre unit of 4 to 6.

* * * * *